US012005196B2

(12) United States Patent
Koda et al.

(10) Patent No.: US 12,005,196 B2
(45) Date of Patent: Jun. 11, 2024

(54) METHOD FOR PRODUCING CATHETER TUBE

(71) Applicant: KANEKA CORPORATION, Osaka (JP)

(72) Inventors: Takuro Koda, Settsu (JP); Hesong Ye, Settsu (JP)

(73) Assignee: KANEKA CORPORATION, Osaka (JP)

( * ) Notice: Subject to any disclaimer, the term of this patent is extended or adjusted under 35 U.S.C. 154(b) by 330 days.

(21) Appl. No.: 17/431,889

(22) PCT Filed: Jan. 21, 2020

(86) PCT No.: PCT/JP2020/001937
§ 371 (c)(1),
(2) Date: Aug. 18, 2021

(87) PCT Pub. No.: WO2020/217609
PCT Pub. Date: Oct. 29, 2020

(65) Prior Publication Data
US 2022/0168541 A1 Jun. 2, 2022

(30) Foreign Application Priority Data

Apr. 24, 2019 (JP) .................................. 2019-082880

(51) Int. Cl.
*A61M 25/00* (2006.01)
*B29C 49/10* (2006.01)
*B29L 31/00* (2006.01)

(52) U.S. Cl.
CPC .... *A61M 25/0009* (2013.01); *A61M 25/0015* (2013.01); *B29C 49/10* (2013.01); *B29C 2793/009* (2013.01); *B29L 2031/7542* (2013.01)

(58) Field of Classification Search
CPC ... B29C 49/10; B29C 33/18; B29C 2791/006; B29C 51/10; B29C 2045/14155;
(Continued)

(56) References Cited

U.S. PATENT DOCUMENTS 5,229,143 A * 7/1993 Ogura .................... B29C 49/56
425/540
2012/0213623 A1 8/2012 Hariki et al.
(Continued)

FOREIGN PATENT DOCUMENTS

JP 2012-171039 A 9/2012

OTHER PUBLICATIONS

International Search Report, issued in PCT/JP2020/001937, dated Mar. 24, 2020.
(Continued)

*Primary Examiner* — Emmanuel S Luk
*Assistant Examiner* — Elisa H Vera
(74) *Attorney, Agent, or Firm* — Birch, Stewart, Kolasch & Birch, LLP

(57) ABSTRACT

The present application relates to a method for producing a catheter tube. The method including sucking gas from a second end 43 of a tubular body 40 while introducing pressurized gas into a lumen 41 of the tubular body 40 from a first end 42 of the tubular body 40, so that an internal pressure is applied to the lumen 41 of the tubular body 40 by introducing the pressurized gas, and the tubular body 40 is delivered in a direction from the first end 42 to the second end 43 by sucking the gas from the second end 43 of the tubular body 40.

20 Claims, 6 Drawing Sheets

(58) Field of Classification Search
CPC ....... B29C 2045/1731; A61M 25/0009; A61M 25/0015; B29L 2031/7542
See application file for complete search history.

(56) References Cited

U.S. PATENT DOCUMENTS

2012/0280432 A1* 11/2012 Chen .................. B29C 49/4273
264/400
2015/0061196 A1* 3/2015 Dachs ..................... B29C 33/10
425/522

OTHER PUBLICATIONS

Written Opinion of the International Searching Authority, issued in PCT/JP2020/001937, dated Mar. 24, 2020.

* cited by examiner

[Fig. 1]
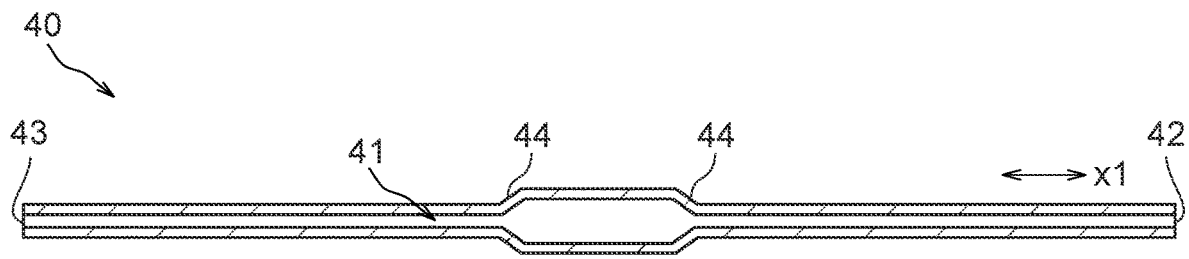
[Fig. 2]
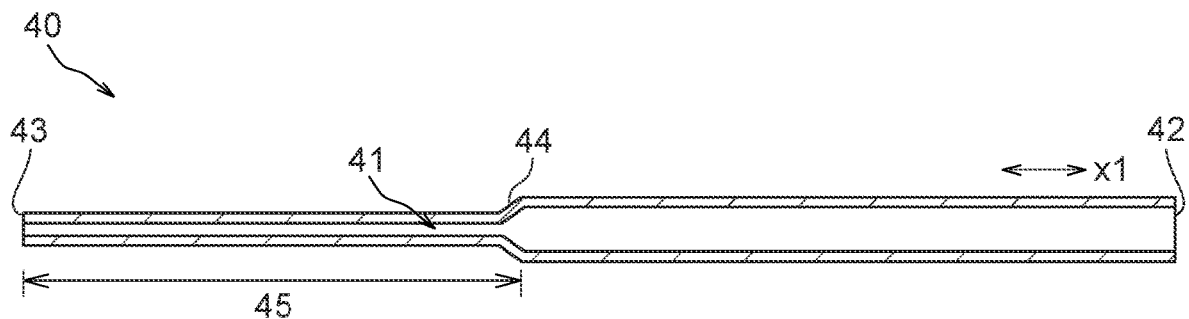
[Fig. 3]

[Fig. 4]
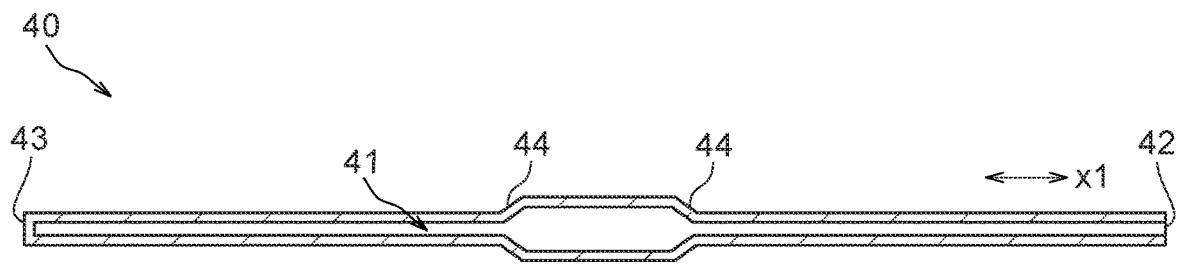
[Fig. 5]
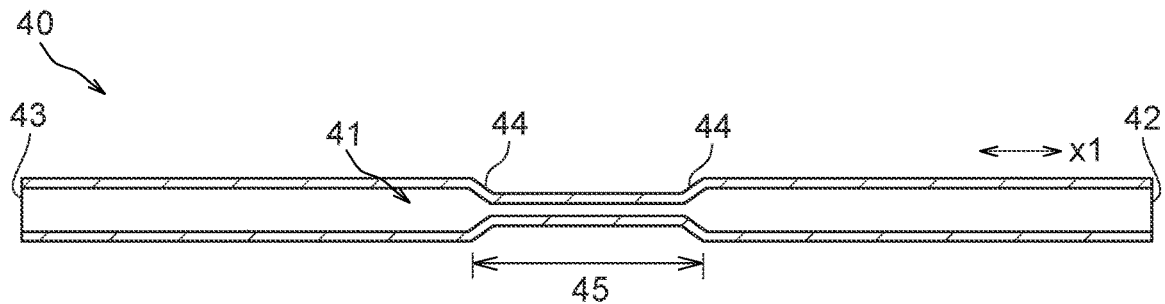
[Fig. 6]
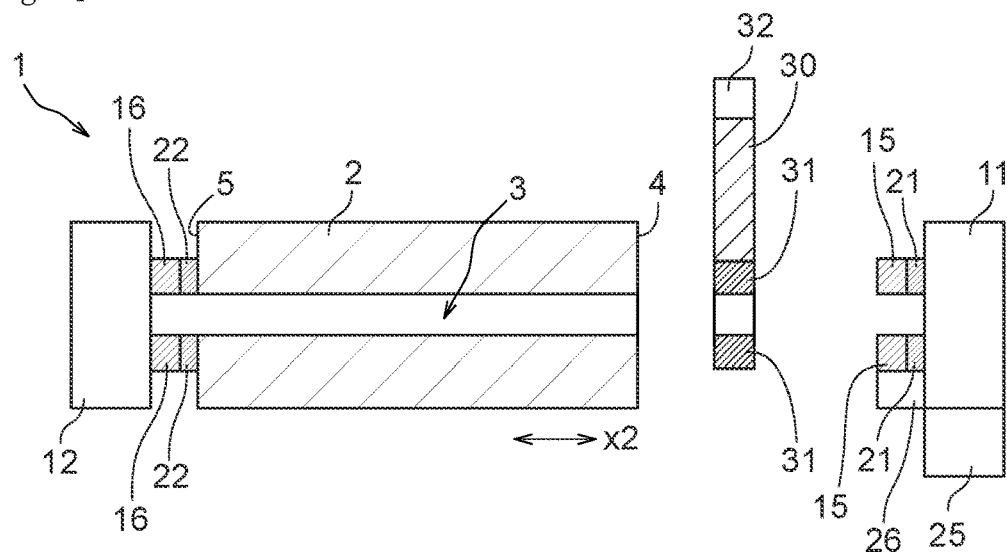

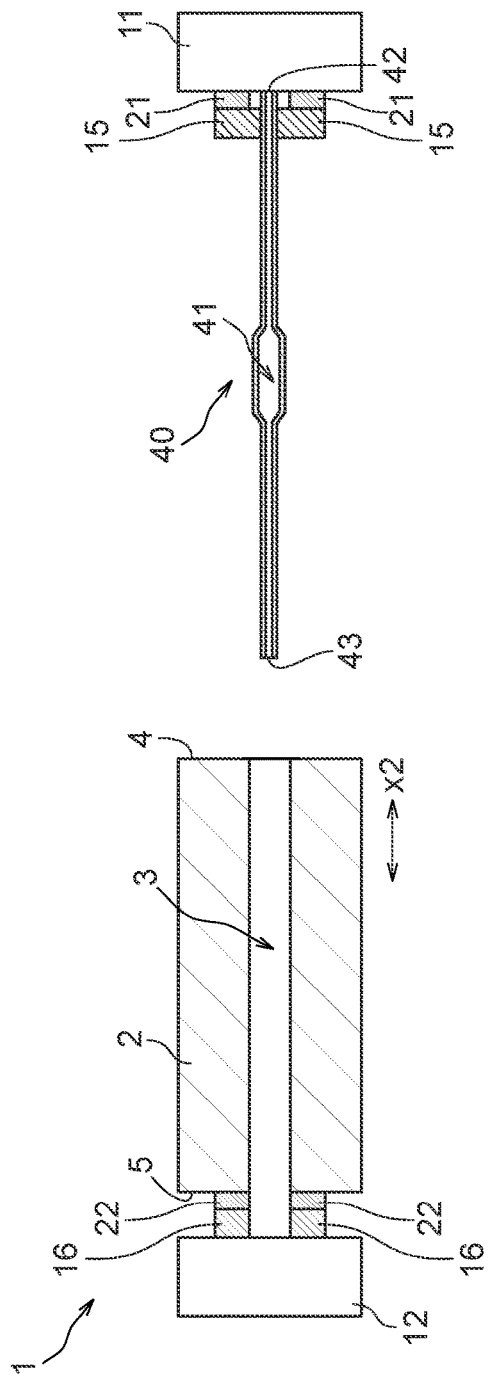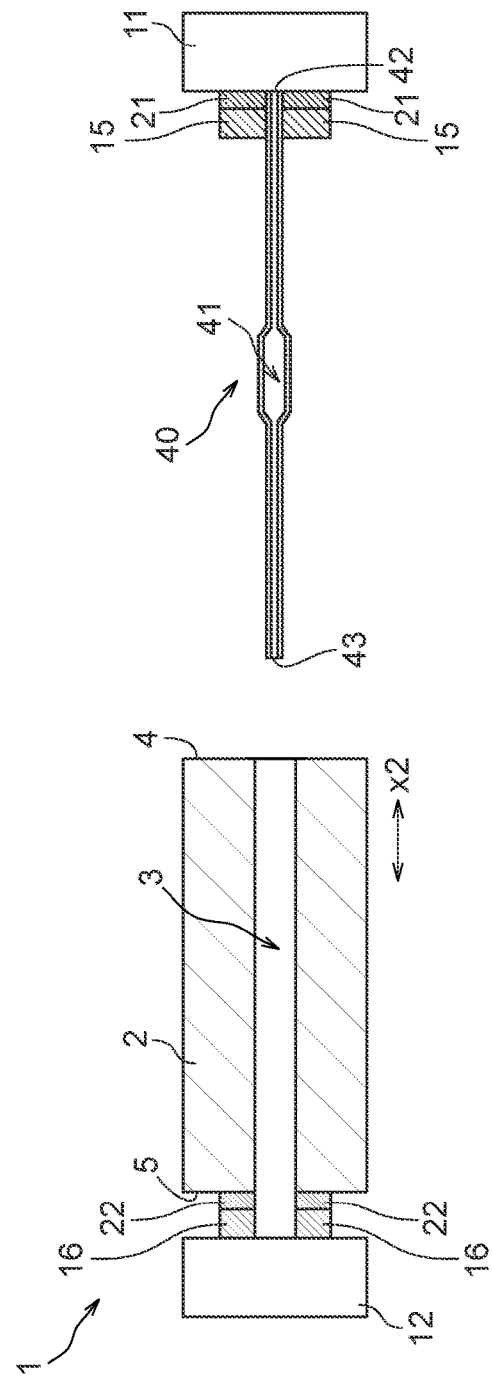

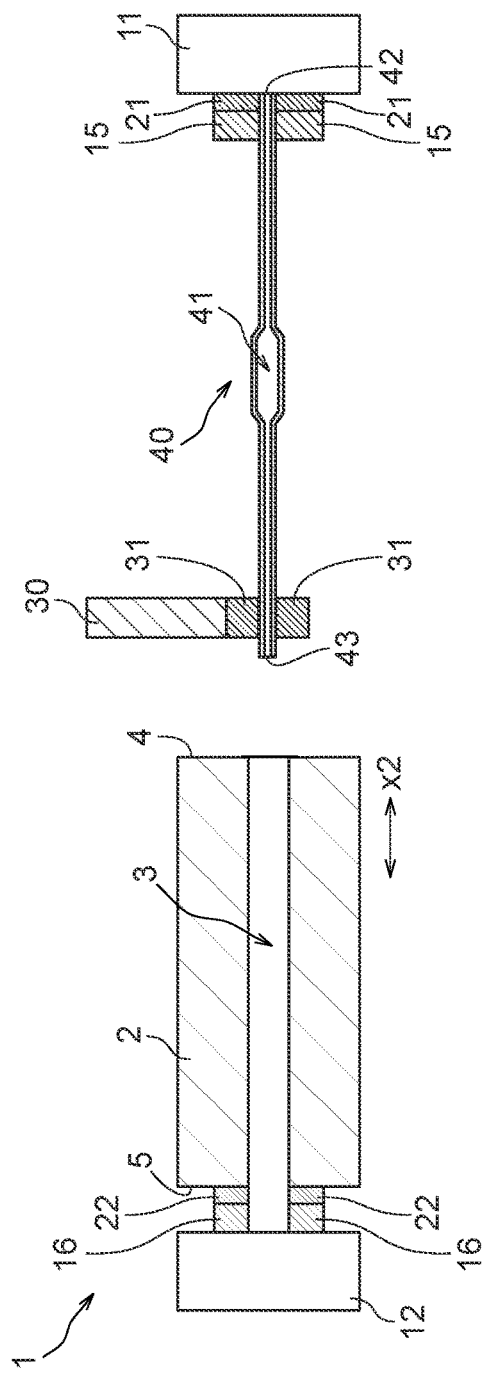
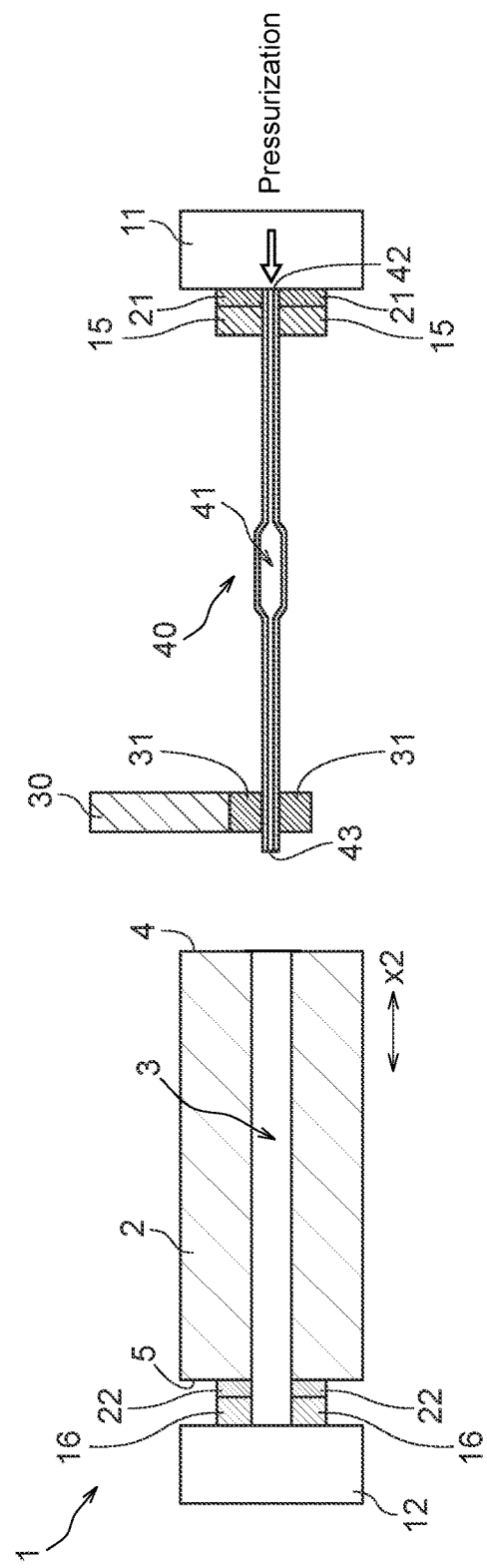

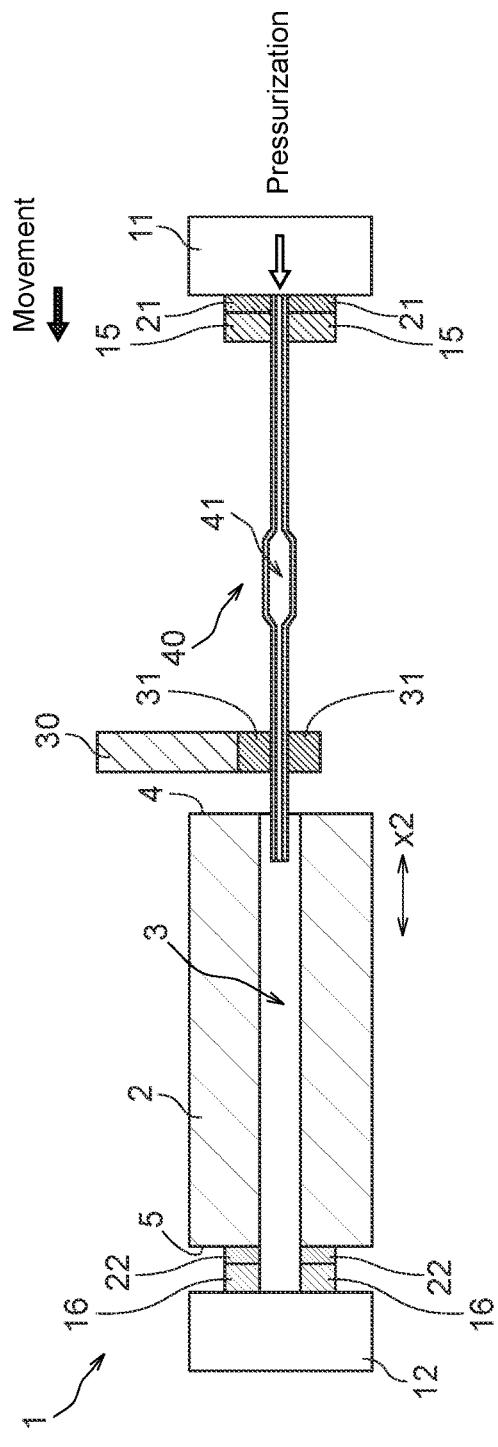
[Fig. 11]
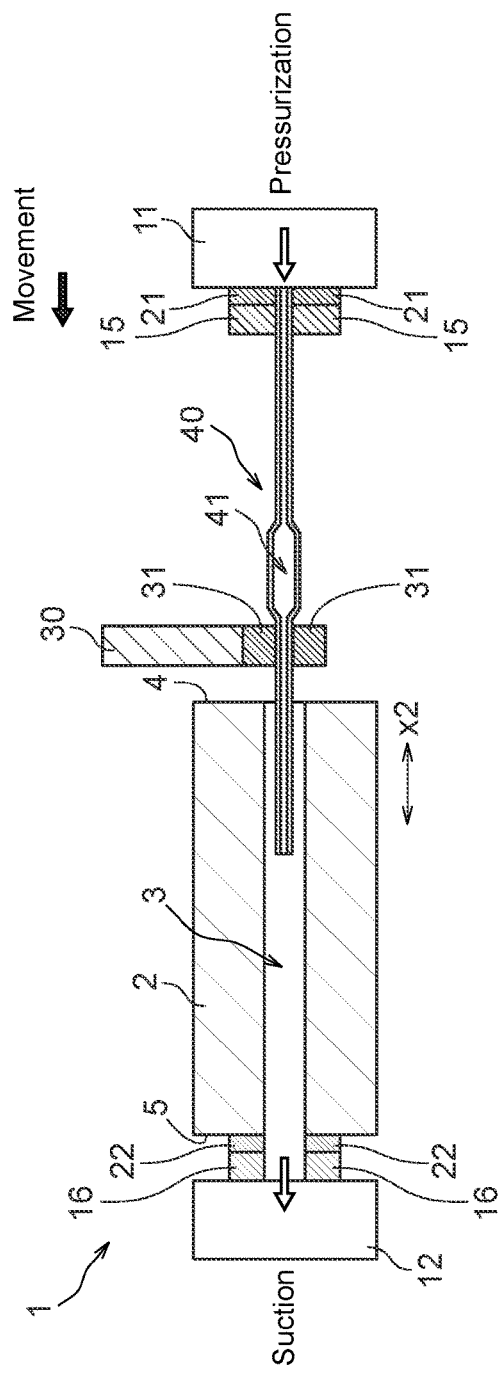
[Fig. 12]

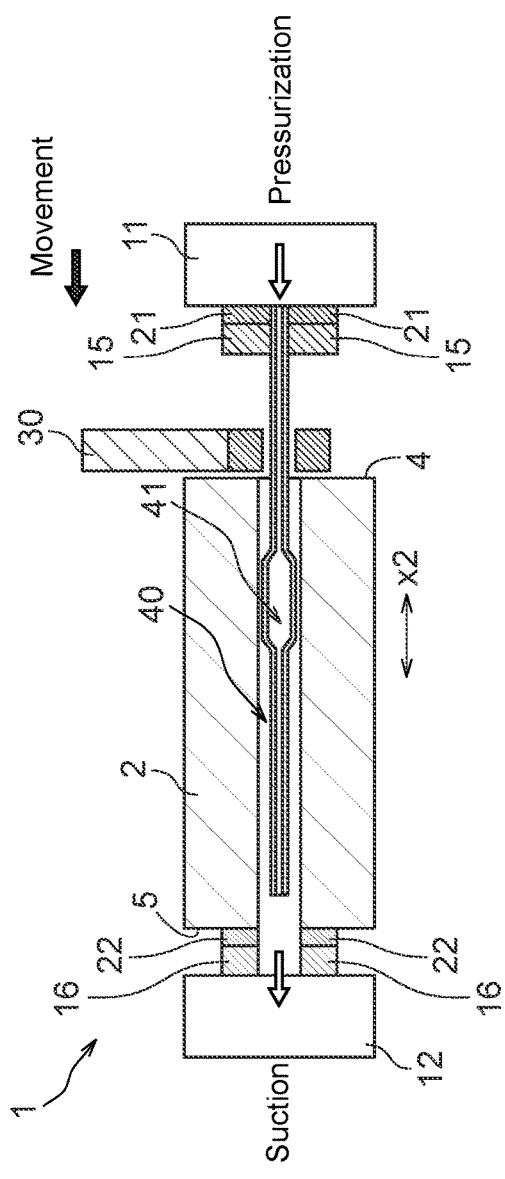
[Fig. 13]
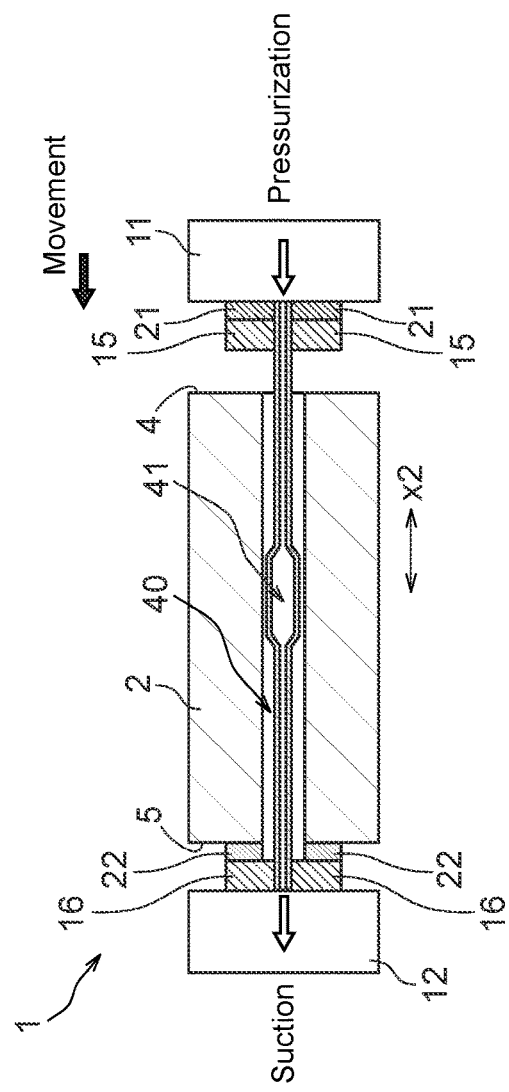
[Fig. 14]

METHOD FOR PRODUCING CATHETER TUBE

TECHNICAL FIELD

The present invention relates to a device configured to deliver a flexible tubular body such as a medical tube, and a method for producing a catheter tube.

BACKGROUND ART

Suction with use of a suction device is exemplified as a method for delivering a target object to a desired position. For example, a delivery device for a bar member is disclosed in Patent Document 1. The delivery device includes a suction device provided with a nozzle configured to suck and hold the bar member. The delivery device raises the nozzle sucking the bar member so as to suck at least part of the bar member into the nozzle, and delivers the bar member being stood to a predetermined place.

RELATED ART DOCUMENTS

Patent Documents

Patent Document 1: JP-A-2012-171039

SUMMARY OF THE INVENTION

Technical Problem

In a case where a flexible tubular body is sucked and delivered, the tubular body is bent or deformed by suction power and thus problematically fails to be disposed at a desired position such as inside a metal mold. The delivery device has been accordingly susceptible to improvement. In view of this, it is an object of the present invention to provide a device configured to suck and deliver a flexible tubular body to a desired position while inhibiting the tubular body from being bent or deformed, as well as a method for producing a catheter tube.

Solutions to the Problems

The gist of one embodiment of a device configured to deliver a flexible tubular body according to the present invention that can overcome the above problems is as follows. The device includes a hollow body having a hollow portion extending from a first end to a second end of the hollow body, a pressure portion disposed at the first end of the hollow body and connected to the tubular body so as to introduce pressurized gas into a lumen of the tubular body, and a negative pressure portion disposed at the second end of the hollow body and connected to the hollow body so as to suck gas from the hollow portion of the hollow body. In the device, the pressure portion introduces pressurized gas into the lumen of the tubular body to apply internal pressure to the tubular body and improve rigidity of the tubular body. The negative pressure portion can thus efficiently suck and deliver, into the hollow portion, the tubular body that is inhibited from being bent or deformed.

Preferably, the device further includes a first holding portion disposed between the pressure portion and the hollow body, the first holding portion holding a first end portion of the tubular body, and a second holding portion disposed between the hollow body and the negative pressure portion, the second holding portion holding a second end portion of the tubular body delivered toward the second end of the hollow body. Preferably, each of the first holding portion and the second holding portion includes one or more chuck pieces.

Preferably, the device further includes a first seal portion disposed between the pressure portion and the first end portion of the tubular body, the first seal portion sealing a gap between the pressure portion and the tubular body, and a second seal portion disposed between the hollow body and the negative pressure portion, the second seal portion sealing a gap between the hollow body and the negative pressure portion.

Preferably, the device further includes a first drive mechanism configured to move at least one of the pressure portion and the first holding portion in an extending direction of the hollow portion.

Preferably, the device further includes a second drive mechanism configured to move at least one of the pressure portion, the first holding portion, and the first seal portion in an extending direction of the hollow portion.

Preferably, at a second end of the tubular body, the gas sucked by the negative pressure portion is larger in amount than gas discharged from the lumen of the tubular body.

Preferably, a difference between a diameter of the hollow portion at the second end of the hollow body and an outer diameter at a second end of the tubular body is larger than a difference between a diameter of the hollow portion at the first end of the hollow body and a maximum outer diameter of the tubular body.

The second end portion of the tubular body may be sealed. Furthermore, the tubular body may has a portion smaller in outer diameter than the first end, the portion being located closer to the second end rather than the first end.

Preferably, the device further includes a support portion disposed between the hollow body and the pressure portion, the support portion supporting the tubular body.

The gist of an embodiment of a method for producing a catheter tube according to the present invention that can overcome the above problems is as follows. A method for producing a catheter tube includes sucking gas from a second end of a tubular body while introducing pressurized gas into a lumen of the tubular body from a first end of the tubular body. Introduction of pressurized gas into the lumen of the tubular body allows to apply internal pressure to the tubular body and improve rigidity of the tubular body. This can thus efficiently suck and deliver, into a desired position, the tubular body that is inhibited from being bent or deformed.

The gist of another embodiment of a method for producing a catheter tube according to the present invention that can overcome the above problems is as follows. A method for producing a catheter tube includes preparing a flexible tubular body having a first end and a second end, sucking gas from the second end of the tubular body while introducing pressurized gas into a lumen of the tubular body from the first end of the tubular body, and performing at least one of pressurization, heating, and stretching of the tubular body. According to the present invention, introduction of pressurized gas into the lumen of the tubular body allows to apply internal pressure to the tubular body and improve rigidity of the tubular body. This can thus efficiently suck and deliver, into a desired position, the tubular body that is inhibited from being bent or deformed. Furthermore, performing at least one of pressurization, heating, and stretching of the tubular body can produce the catheter tube having a desired shape.

The gist of yet another embodiment of a method for producing a catheter tube according to the present invention that can overcome the above problems is as follows. A method for producing a catheter tube includes preparing a tubular body having a first end and a second end, the second end being sealed, sucking gas from the second end of the tubular body while introducing pressurized gas into a lumen of the tubular body from the first end of the tubular body, performing at least one of pressurization, heating, and stretching of the tubular body, and cutting a second end portion of the tubular body to allow the lumen at the second end to communicate with an outside of the tubular body. According to the present invention, introduction of pressurized gas into the lumen of the tubular body allows to apply internal pressure to the tubular body and improve rigidity of the tubular body. This can thus efficiently suck and deliver, into a desired position, the tubular body that is inhibited from being bent or deformed. Furthermore, performing at least one of pressurization, heating, and stretching of the tubular body can produce the catheter tube having a desired shape. Moreover, cutting the second end portion of the tubular body having the second end sealed allow the lumen at the second end of the tubular body to communicate with an outside, the tube thus produced can have the lumen penetrating from the first end to the second end.

The present invention provides a method for producing a catheter tube using a device configured to deliver a flexible tubular body, the device including the hollow body, the pressure portion, the negative pressure portion, the first holding portion, the second holding portion, the first seal portion, and the second seal portion. The method includes holding the first end portion of the tubular body with the first holding portion, sealing a gap between the first holding portion and the tubular body with the first seal portion, connecting the pressure portion to a first end of the tubular body and introducing pressurized gas into the lumen of the tubular body with the pressure portion, sealing the gap between the hollow body and the negative pressure portion with the second seal portion, moving the pressure portion and the tubular body toward the hollow portion so that a part of the tubular body is disposed in the hollow portion, sucking gas in the hollow portion of the hollow body with the negative pressure portion so that the tubular body is delivered toward the second end of the hollow body, and holding the second end portion of the tubular body with the second holding portion. According to the present invention, the pressure portion introduces pressurized gas into the lumen of the tubular body to apply internal pressure to the tubular body and improve rigidity of the tubular body. The negative pressure portion can thus efficiently suck and deliver, into the hollow portion, the tubular body that is inhibited from being bent or deformed.

Advantageous Effects of the Invention

According to the present invention, introduction of pressurized gas into the lumen of the tubular body allows to apply internal pressure to the tubular body and improve rigidity of the tubular body. This can thus efficiently suck and deliver, into a desired position, the tubular body that is inhibited from being bent or deformed.

BRIEF DESCRIPTION OF THE DRAWINGS

FIG. 1 is a sectional view of a flexible tubular body according to an embodiment of the present invention.

FIG. 2 is a sectional view according to a modification example, of the tubular body depicted in FIG. 1.

FIG. 3 is a sectional view according to another modification example, of the tubular body depicted in FIG. 1.

FIG. 4 is a sectional view according to still another modification example, of the tubular body depicted in FIG. 1.

FIG. 5 is a sectional view according to still another modification example, of the tubular body depicted in FIG. 1.

FIG. 6 is a sectional view (partially side view) of a delivery device according to an embodiment of the present invention.

FIG. 7 is a sectional view (partially side views) indicating a method of producing a catheter tube according to an embodiment of the present invention.

FIG. 8 is a sectional view (partially side views) indicating a method of producing a catheter tube according to an embodiment of the present invention.

FIG. 9 is a sectional view (partially side views) indicating a method of producing a catheter tube according to an embodiment of the present invention.

FIG. 10 is a sectional view (partially side views) indicating a method of producing a catheter tube according to an embodiment of the present invention.

FIG. 11 is a sectional view (partially side views) indicating a method of producing a catheter tube according to an embodiment of the present invention.

FIG. 12 is a sectional view (partially side views) indicating a method of producing a catheter tube according to an embodiment of the present invention.

FIG. 13 is a sectional view (partially side views) indicating a method of producing a catheter tube according to an embodiment of the present invention.

FIG. 14 is a sectional view (partially side views) indicating a method of producing a catheter tube according to an embodiment of the present invention.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

An embodiment of a device configured to deliver a flexible tubular body according to the present invention includes a hollow body having a hollow portion extending from a first end to a second end of the hollow body, a pressure portion disposed at the first end of the hollow body and connected to the tubular body so as to introduce pressurized gas into a lumen of the tubular body, and a negative pressure portion disposed at the second end of the hollow body and connected to the hollow body so as to suck gas from the hollow portion of the hollow body. In the device, the pressure portion introduces pressurized gas into the lumen of the tubular body to apply internal pressure to the tubular body and improve rigidity of the tubular body. The negative pressure portion can thus efficiently suck and deliver, into the hollow portion, the tubular body that is inhibited from being bent or deformed.

Description is initially made to a tubular body as a delivery target with reference to FIGS. 1 to 5. FIG. 1 is a longitudinal sectional view of a tubular body according to an embodiment of the present invention, and FIGS. 2 to 5 are sectional views according to a modification example, of the tubular body depicted in FIG. 1. A tubular body 40 is a member to be processed into an industrial or medial tube, preferably a catheter tube. The tubular body 40 has flexibility. The tubular body 40 preferably has elasticity so as to be kept in shape. The tubular body 40 has a first end 42 and a second end 43, and extends in a longitudinal direction x1 from the first end 42 to the second end 43. The tubular body 40 has a lumen 41 into which a pressure portion 11 to be described later introduces pressurized gas. Gas is sucked from the second end 43 of the tubular body 40 by a negative pressure portion 12 to be described later.

The tubular body 40 is preferred to have a length in the longitudinal direction x1 larger than a length of an outer circumference. The tubular body 40 is not particularly limited in terms of its length, and may be 10 cm or more, 20 cm or more, 30 cm or more, or the like. The tubular body 40 is preferably 200 cm or less, 150 cm or less, or 100 cm or less for easier suction. The tubular body 40 is not particularly limited in terms of its sectional shape, and can have a circular shape, an oblong shape, a polygonal shape, a shape obtained by combining any of these shapes, or the like. Examples of the oblong shape include an elliptical shape, an oval shape, and a rectangular shape having rounded corners. For easier suction, the tubular body 40 has an outer diameter exemplarily preferred to be 0.1 mm or more, 0.5 mm or more, or 1 mm or more, and preferred to be 30 mm or less, 20 mm or less, or 10 mm or less. The device can be changed in size in accordance with the length and the outer diameter of the tubular body.

The outer diameter of the tubular body 40 may be varied in the longitudinal direction x1. The tubular body 40 may exemplarily have a tapered portion or a stepped portion that is reduced, toward the first end 42 or the second end 43, in at least one of the outer diameter and an inner diameter. In FIGS. 1, 2, 4, and 5, the tubular body 40 has a tapered portion 44. As depicted in FIGS. 2 and 5, the tubular body 40 preferably has a portion 45 (hereinafter, referred to as a small diameter portion 45) which is smaller in outer diameter than the first end 42 of the tubular body 40 and disposed closer to the second end 43 rather than the first end 42. The tubular body 40 thus configured facilitates suction because discharge of gas from the second end 43 of the tubular body 40 is inhibited even when the pressure portion 11 introduces pressurized gas into the lumen 41 of the tubular body 40. The small diameter portion 45 thus configured has only to be disposed closer to the second end 43 rather than the first end 42 of the tubular body 40, and may be disposed at the second end 43 of the tubular body 40. The device according to the present invention can efficiently deliver the tubular body 40 regardless of the shape exemplified in each of FIGS. 1 to 5.

In view of inhibition of deformation such as expansion of the tubular body 40 due to application of excessive internal pressure, the lumen 41 of the tubular body 40 preferably penetrates from the first end 42 to the second end 43 as depicted in FIGS. 1 to 3 and 5. As depicted in FIG. 4, the tubular body 40 has a second end portion that may be sealed. In this configuration, gas is not discharged from the second end 43 of the tubular body 40 even when the pressure portion 11 introduces pressurized gas into the lumen 41 of the tubular body 40, so that the pressure portion 11 can easily apply pressure and the negative pressure portion 12 can easily suck gas from the second end 43 of the tubular body 40.

The tubular body 40 is made of a material that can be a resin or a metal. Examples of the resin contained in the tubular body 40 include a polyamide resin, a polyester resin, a polyurethane resin, a polyolefin resin, a fluororesin, a vinyl chloride resin, a silicone resin, and natural rubber. The tubular body 40 may contain only one of these resins, or two or more of these resins. Examples of the metal contained in the tubular body 40 include stainless steel such as SUS304 or SUS316, platinum, nickel, cobalt, chromium, titanium, tungsten, gold, Ni—Ti alloy, Co—Cr alloy, or a combination of any of these. In particular, the tubular body 40 is preferably a resin tube, and is more preferably a fluororesin tube or a polyamide resin tube. The tubular body 40 as a resin tube can be produced by extrusion molding or the like. The tubular body 40 may have a single layer, or may have a plurality of layers at least partially in the longitudinal direction x1. The tubular body 40 may alternatively be a coil of a spirally wound linear member made of a resin or a metal. Furthermore, the coil has an outer surface and an inner surface at least one of which may be covered with a resin. The tubular body 40 has only to be flexible, and is preferably improved in rigidity of the entire tubular body 40 when pressurized particularly from an end portion in the longitudinal direction x1.

The device configured to deliver the tubular body 40 (hereinafter, occasionally referred to as a "delivery device 1") will be described with reference to FIG. 6. The delivery device 1 is preferred to deliver tubular bodies 40 one by one, but may alternatively deliver a plurality of tubular bodies collectively. The delivery device 1 includes a hollow body 2, the pressure portion 11, and the negative pressure portion 12.

The hollow body 2 has a first end 4 and a second end 5, and includes a hollow portion 3 extending from the first end 4 to the second end 5. In other words, the hollow portion 3 is provided to penetrate from the first end 4 to the second end 5 of the hollow body 2. The negative pressure portion 12 to be described later causes gas to flow from the first end 4 to the second end 5 in the hollow portion 3, so that the tubular body 40 disposed at the first end 4 of the hollow portion 3 is drawn into the hollow portion 3 via the first end 4 of the hollow body 2. Hereinafter, a direction from the first end 4 to the second end 5 of the hollow body 2 will be referred to as an extending direction x2 of the hollow portion 3. The extending direction of the hollow portion 3 may match a longitudinal direction of the hollow body 2 or may differ from the longitudinal direction of the hollow body 2.

The hollow body 2 preferably has a tubular shape, and can have an oblong cylindrical shape such as a cylindrical shape or an elliptic cylindrical shape, a polygonal tubular shape, or the like. The hollow body 2 is preferred to be a metal mold. This configuration enables processing such as heat stretching or blow molding of the tubular body 40 delivered into the hollow portion 3 in the hollow body 2. The hollow body 2 can exemplarily serve as a first metal mold that is included in a metal mold dividable into a plurality of parts in the longitudinal direction x1 and is disposed closest to the second end 5. After the device according to the present invention delivers the tubular body 40 into the hollow body 2 (the first metal mold), the hollow body and a different metal mold (e.g. a second metal mold disposed closer to the first end 4 in comparison to the first metal mold) may be coupled integrally so as to be preferably used for blow molding.

The extending direction x2 of the hollow portion 3 in the hollow body 2 may match a horizontal direction or a vertical direction, or may differ from the horizontal direction or the vertical direction. As exemplarily depicted in FIG. 6, the extending direction x2 of the hollow portion 3 may match a horizontal direction x perpendicular to a vertical direction y. The tubular body 40 drawn into the hollow portion 3 thus moves in the horizontal direction x and can be easily controlled in terms of its moving direction. Though not depicted, the extending direction x2 of the hollow portion 3 may slant from the horizontal direction x. For example, the first end 4 of the hollow body 2 may be disposed above the second end 5 in the vertical direction y. More specifically, the extending direction x2 of the hollow portion 3 may slant from the horizontal direction x by five degrees or more, ten degrees or more, or 15 degrees or more, and may slant by 60 degrees or less, 55 degrees or less, or 50 degrees or less. This configuration can utilize gravity for delivery of the tubular body 40 and enables quick delivery of the tubular body 40. The longitudinal direction x1 of the tubular body 40 and the extending direction x2 of the hollow portion 3 in the hollow body 2 are preferred to match each other, but may alternatively differ from each other. When the longitudinal direction x1 of the tubular body 40 and the extending direction x2 of the hollow portion 3 in the hollow body 2 cross each other, these directions form a crossing angle that is preferably within the above range in view of delivery efficiency.

The hollow portion 3 has a diameter that may be constant entirely in the extending direction x2 of the hollow portion 3, or may be varied. In order to easily insert the tubular body 40 into the hollow body 2, the hollow portion 3 has an inlet portion that is disposed at the first end 4 of the hollow body 2 and preferably has a funnel shape gradually narrowed from the inlet portion toward the lumen. At the first end portion 4 of the hollow body 2, the diameter of the hollow portion 3 is preferably reduced toward the second end 5. In order to suck the tubular body 40 into the hollow body 2 more efficiently, the diameter of the hollow portion 3 at the second end 5 of the hollow body 2 is preferably larger than the diameter of the hollow portion 3 at the first end 4 of the hollow body 2.

The hollow body 2 is preferably made of a metal. Examples of the metal contained in the hollow body 2 include stainless steel such as SUS304 or SUS316, platinum, nickel, cobalt, chromium, titanium, tungsten, gold, Ni—Ti alloy, Co—Cr alloy, or a combination of any of these.

The pressure portion 11 is disposed at the first end 4 of the hollow body 2 and is connected to the tubular body 40 so as to introduce pressurized gas into the lumen 41 of the tubular body 40. The pressure portion 11 introduces pressurized gas into the lumen 41 of the tubular body 40 so as to apply internal pressure to the tubular body 40 and improve rigidity of the tubular body 40. The negative pressure portion 12 can thus efficiently suck and deliver, into the hollow portion 3, the tubular body 40 that is inhibited from being bent or deformed.

The pressure portion 11 is connected to the tubular body 40 and introduces pressurized gas into the lumen 41 of the tubular body 40. The pressure portion 11 has only to have a function of pressure sending gas, and examples thereof include a compressor and a booster pump. Pressurized gas is not particularly limited in terms of its type, and examples thereof can include nitrogen, helium, argon, and air.

The pressure portion 11 is preferably connected to a side of the tubular body 40, and is more preferably connected to a first end portion of the tubular body 40. The pressure portion 11 may be connected directly to the tubular body 40, or may be connected to the tubular body 40 via a tube such as a hose or pipe, or a joint.

The negative pressure portion 12 is disposed at the second end 5 of the hollow body 2 and is connected to the hollow body 2 so as to suck gas from the hollow portion 3 in the hollow body 2. The negative pressure portion 12 sucks gas in the hollow portion 3 from the second end 5 of the hollow body 2 to cause the hollow portion 3 to have negative pressure lower than the atmospheric pressure, so that gas flows from the first end 4 to the second end 5 in the hollow portion 3. The tubular body 40 is thus drawn into the hollow portion 3 via the first end 4 of the hollow body 2. The negative pressure portion 12 has only to have a function of sucking gas, and examples thereof include a suction device and a vacuum pump. The negative pressure portion 12 sucks air in the hollow portion 3, as well as gas introduced by the pressure portion 11 into the lumen 41 of the tubular body 40 and discharged from the second end 5.

The negative pressure portion 12 may be connected directly to the hollow body 2, or may be connected to the hollow body 2 via a tube such as a hose or pipe, a joint, or a different member. FIG. 6 exemplifies the negative pressure portion 12 connected to the hollow body 2 via a second holding portion 16 to be described later.

At the second end 43 of the tubular body 40, gas sucked by the negative pressure portion 12 is preferably larger in amount than gas discharged from the lumen 41 of the tubular body 40. The amount of sucked gas and the amount of discharged gas at the second end 43 of the tubular body 40 are set in this manner to enable the negative pressure portion 12 to suck gas from the tubular body 40.

A difference between the diameter of the hollow portion 3 at the second end 5 of the hollow body 2 and the outer diameter at the second end 43 of the tubular body 40 is preferably larger than a difference between the diameter of the hollow portion 3 at the first end 4 of the hollow body 2 and a maximum outer diameter of the tubular body 40, is more preferably larger by 1.5 times or more, and is further preferably larger by two times or more. The outer diameter of the tubular body 40 is set in this manner to facilitate suction of gas from the second end 43 of the tubular body 40.

The delivery device 1 may further include a first holding portion 15 disposed between the pressure portion 11 and the hollow body 2 and holding the first end portion of the tubular body 40. The first holding portion 15 holds the tubular body 40 to facilitate introduction of pressurized gas into the lumen 41 of the tubular body 40.

The first holding portion 15 holds at a position not particularly limited as long as being located in the first end portion of the tubular body 40. The position is preferably located within 10 cm from the first end 42 of the tubular body 40 in the longitudinal direction x1, is more preferably located within 8 cm, and is further preferably located within 5 cm.

The delivery device 1 may further include the second holding portion 16 disposed between the hollow body 2 and the negative pressure portion 12 and holding the second end portion of the tubular body 40 delivered toward the second end 5 of the hollow body 2. The second holding portion 16 holds the tubular body 40 to facilitate processing such as stretching or expanding of the tubular body 40 in a subsequent step.

The second holding portion 16 holds at a position not particularly limited as long as being located in the second end portion of the tubular body 40. The position is preferably located within 10 cm from the second end 43 of the tubular body 40 in the longitudinal direction x1, is more preferably located within 8 cm, and is further preferably located within 5 cm.

The first holding portion 15 or the second holding portion 16 has only to include a mechanism configured to hold and release the tubular body 40. For example, the first holding portion 15 or the second holding portion 16 preferably includes a single or a plurality of chuck pieces, and each of the first holding portion 15 and the second holding portion 16 more preferably includes a single or a plurality of chuck pieces. Such a chuck piece can accurately hold the tubular body 40. Though not depicted, the first holding portion 15 or the second holding portion 16 may include two chuck pieces facing each other and configured to pinch the tubular body 40. The holding mechanisms of the first holding portion 15 and the second holding portion 16 may be configured identically or differently from each other.

The first holding portion 15 or the second holding portion 16 is made of a metal material or an elastic material, and reference can be made to description of the material for the hollow body 2 and the material for the tubular body 40. In order to prevent damage on an outer surface of the tubular body 40, the first holding portion 15 or the second holding portion 16 has a portion that is in contact with the tubular body 40 and may be provided with an elastic body.

The delivery device 1 is preferred to further include a first seal portion 21 disposed between the pressure portion 11 and the first end portion of the tubular body 40 and sealing a gap between the pressure portion 11 and the tubular body 40. The gap between the pressure portion 11 and the tubular body 40 is thus sealed to reduce leakage of gas during introduction of pressurized gas into the tubular body 40.

The delivery device 1 is preferred to further include a second seal portion 22 disposed between the hollow body 2 and the negative pressure portion 12 and sealing a gap between the hollow body 2 and the negative pressure portion 12. The gap between the hollow body 2 and the negative pressure portion 12 is thus sealed to reduce leakage of gas during suction by the negative pressure portion 12.

The first seal portion 21 or the second seal portion 22 can be an elastic seal member such as a gasket or a packing. The seal member can be made of natural rubber, synthetic rubber such as a styrene-butadiene copolymer, a synthetic resin such as polyurethane. The seal member may have a ring shape, a sheet shape, a tape shape, or the like. The first seal portion 21 and the second seal portion 22 may be of an identical type or may be of different types.

The first holding portion 15 may also serve as the first seal portion 21. Furthermore, the second holding portion 16 may also serve as the second seal portion 22. Moreover, a chuck piece may also serve as a seal portion. The first holding portion 15 or the second holding portion 16 may be constituted by an elastic member in order to also function as a seal portion as mentioned above. The holding portion thus configured holds the tubular body 40 to seal the gap between the pressure portion 11 and the tubular body 40 or the gap between the hollow body 2 and the negative pressure portion 12.

The delivery device 1 preferably includes a first drive mechanism configured to move at least one of the pressure portion 11 and the first holding portion 15 in the extending direction x2 of the hollow portion 3. The negative pressure portion 12 sucks to move the tubular body 40. When the first drive mechanism is provided, at least one of the pressure portion 11 and the first holding portion 15 can be moved along with movement of the tubular body 40. Accordingly, pressurized gas can be introduced into the lumen 41 of the tubular body 40 during suction by the negative pressure portion 12. FIG. 6 exemplarily depicts a first drive mechanism 25 configured to move the pressure portion 11 in the extending direction x2 of the hollow portion 3.

The delivery device 1 preferably includes a second drive mechanism configured to move at least one of the pressure portion 11, the first holding portion 15, and the first seal portion 21 in the extending direction x2 of the hollow portion 3. The negative pressure portion 12 sucks to move the tubular body 40. When the second drive mechanism is provided, at least one of the pressure portion 11, the first holding portion 15, and the first seal portion 21 can be moved along with movement of the tubular body 40. Accordingly, pressurized gas can be introduced into the lumen 41 of the tubular body 40 during suction by the negative pressure portion 12. FIG. 6 exemplarily depicts a second drive mechanism 26 configured to move the first holding portion 15 and the first seal portion 21 in the extending direction x2 of the hollow portion 3.

The delivery device 1 may include both the first drive mechanism and the second drive mechanism, or may include either one of the first drive mechanism and the second drive mechanism. As exemplarily depicted in FIG. 6, the delivery device 1 may include the first drive mechanism 25 configured to move the pressure portion 11, and the second drive mechanism 26 configured to move the first holding portion 15 and the first seal portion 21. The delivery device 1 according to another embodiment may include a first drive mechanism configured to move the pressure portion 11 and the first holding portion 15, and a second drive mechanism configured to move the first seal portion 21. The delivery device 1 according to still another embodiment may include a first drive mechanism configured to move the first holding portion 15, and a second drive mechanism configured to move the pressure portion 11 and the first seal portion 21.

The first drive mechanism and the second drive mechanism may be configured identically or differently from each other. The second drive mechanism is preferably configured to move all the pressure portion 11, the first holding portion 15, and the first seal portion 21 in the extending direction x2 of the hollow portion 3. In the state where the first seal portion 21 seals the gap between the pressure portion 11 and the tubular body 40, the pressure portion 11 and the first holding portion 15 can be moved along with movement of the tubular body 40.

The first drive mechanism may exemplarily include a first rail extending in the extending direction x2 of the hollow portion 3, a first delivery portion disposed on the first rail and holding at least one of the pressure portion 11 and the first holding portion 15, and a first controller connected to the first delivery portion and configured to control movement of the first delivery portion. Similarly, the second drive mechanism may exemplarily include a second rail extending in the extending direction x2 of the hollow portion 3, a second delivery portion disposed on the second rail and holding at least one of the pressure portion 11, the first holding portion 15, and the first seal portion 21, and a second controller connected to the second delivery portion and configured to control movement of the second delivery portion.

The first delivery portion or the second delivery portion preferably includes an at least uniaxial actuator configured to drive in the extending direction x2 of the hollow portion 3, more preferably includes a biaxial actuator configured to drive in the extending direction x2 of the hollow portion 3 as well as in one of directions perpendicular to the extending direction x2, and further preferably includes a triaxial actuator configured to drive in the extending direction x2 of the hollow portion 3 as well as in two of the directions perpendicular to the extending direction x2. The delivery portion thus configured enables attachment of the pressure portion 11, the first holding portion 15, or the first seal portion 21 to a robot hand and achieves a highly free design. The actuator includes mechanical elements such as a motor, linear motion guide, a ball screw, a synchronous belt pulley, a slider, and a rack and pinion.

Each of the first controller and the second controller can be exemplarily constituted by an electronic circuit unit including a microcontroller provided at least with a CPU and a memory.

The delivery device 1 is preferred to further include a support portion 30 disposed between the hollow body 2 and the pressure portion 11 and supporting the tubular body 40. The tubular body 40 supported by the support portion 30 is prevented from hanging down due to own weight of the tubular body 40.

Similarly to the first holding portion 15 or the second holding portion 16, the support portion 30 may include a single or a plurality of chuck pieces, or may include two chuck pieces facing each other. Though not depicted, the support portion 30 may alternatively be constituted by a surface provided at a fulcrum disposed below the tubular body 40 in the vertical direction, the surface allowing part of the tubular body 40 in the longitudinal direction x1 to be disposed thereon. The support portion 30 may still alternatively be constituted by a recess provided in the fulcrum and accommodating part of the tubular body 40 in the longitudinal direction x1. FIG. 6 exemplarily depicts the support portion 30 including two chuck pieces 31. As to a material for the support portion 30, reference can be made to description of the material for the hollow body 2.

The delivery device 1 preferably includes a third drive mechanism 32 configured to move the support portion 30 in at least the vertical direction and the extending direction x2 of the hollow portion 3. The third drive mechanism 32 is configured to move the support portion 30 in the extending direction x2 of the hollow portion 3, and the support portion 30 can thus be moved along with movement of the tubular body 40, so as to prevent the tubular body 40 from hanging down due to own weight. The third drive mechanism 32 is also configured to move the support portion 30 in the vertical direction, and can thus withdraw the support portion 30 not in use.

The third drive mechanism 32 may include a third delivery portion connected to the support portion 30, and a third controller connected to the third delivery portion and configured to control movement of the third delivery portion. As to the third delivery portion and the third controller, reference can made to description of the first delivery portion and the second delivery portion, as well as the first controller and the second controller, respectively.

Described hereinafter are first to fourth methods of producing a catheter tube.

The first production method includes sucking gas from a second end 43 of a tubular body 40 while introducing pressurized gas into a lumen 41 of the tubular body 40 from a first end 42 of the tubular body 40. Introduction of gas and suction may start at an identical timing or different timings. In a case where only suction starts when the tubular body 40 approaches the hollow portion 3 in the hollow body 2, the tubular body 40 may be deformed by suction pressure. Accordingly, gas is preferably sucked from the second end 43 of the tubular body 40 after pressurized gas is introduced into the lumen 41 of the tubular body 40.

The second production method includes preparing a flexible tubular body 40 having a first end 42 and a second end 43, sucking gas from the second end 43 of the tubular body 40 while introducing pressurized gas into a lumen 41 of the tubular body 40 from the first end 42 of the tubular body 40, and performing at least one of pressurization, heating, and stretching of the tubular body 40.

The third production method includes preparing a tubular body 40 having a first end 42 and a second end 43, the second end 43 being sealed, sucking gas from the second end 43 of the tubular body 40 while introducing pressurized gas into a lumen 41 of the tubular body 40 from the first end 42 of the tubular body 40, performing at least one of pressurization, heating, and stretching of the tubular body 40, and cutting a second end portion of the tubular body 40 to allow the lumen 41 at the second end 43 to communicate with an outside of the tubular body 40.

In the first to third production methods, introduction of pressurized gas into the lumen 41 of the tubular body 40 allows to apply internal pressure to the tubular body 40 and improve rigidity of the tubular body 40. This can thus efficiently suck and deliver, into a desired position, the tubular body 40 that is inhibited from being bent or deformed. When the third production method includes cutting the second end portion of the tubular body 40 sealed at the second end 43 to allow the lumen at the second end 43 of the tubular body 40 to communicate with an outside, the tube thus produced can have the lumen penetrating from the first end to the second end.

In the first to third production methods, pressurized gas can be introduced into the lumen 41 of the tubular body 40 by the pressure portion 11 described earlier. Gas can be sucked from the second end 43 of the tubular body 40 by the negative pressure portion 12 described earlier.

In a step of performing at least one of pressurization, heating, and stretching of the tubular body 40 in the second or third production method, the tubular body 40 is preferably stretched in at least one of the longitudinal direction x1 and a radial direction. The catheter tube thus produced can have a desired shape. Any one of stretching in the longitudinal direction x1 and stretching in the radial direction may precede, or both may be performed simultaneously. The tubular body 40 may be stretched only once or a plurality of times. In the step of performing at least one of pressurization, heating, and stretching of the tubular body 40, these processes may be performed separately or in combination. Examples of such a step include blow molding.

The tubular body 40 adopted in the third production method preferably has the lumen communicating with an outside at the first end 42. The tubular body 40 thus configured enables introduction of pressurized gas from the first end 42.

In a step of cutting the second end portion of the tubular body 40 in the third production method, the tubular body 40 is preferably cut in a direction perpendicular to the longitudinal direction x1, or may alternatively be cut obliquely to the longitudinal direction x1.

In the third production method, the second end 43 of the tubular body 40 is preferably smaller in outer diameter than the first end 42. The tubular body 40 thus configured facilitates suction from the second end 43 as well as facilitates cutting of the second end portion of the tubular body 40.

In the third production method, the tubular body 40 can be cut with use of a cutter such as a knife, a razor, or scissors.

The fourth production method is a method for producing a catheter tube using a device configured to deliver a flexible tubular body 40, the device including the hollow body 2, the pressure portion 11, the negative pressure portion 12, the first holding portion 15, the second holding portion 16, the first seal portion 21, and the second seal portion 22. The method includes holding the first end portion of the tubular body 40 with the first holding portion 15, sealing a gap between the first holding portion 15 and the tubular body 40 with the first seal portion 21, connecting the pressure portion 11 to a first end 42 of the tubular body 40 and introducing pressurized gas into a lumen 41 of the tubular body 40 with the pressure portion 11, sealing the gap between the hollow body 2 and the negative pressure portion 12 with the second seal portion 22, moving the pressure portion 11 and the tubular body 40 toward the hollow portion 3 so that a part of the tubular body 40 is disposed in the hollow portion 3, sucking gas in the hollow portion 3 of the hollow body 2 with the negative pressure portion 12 so that the tubular body 40 is delivered toward the second end 5 of the hollow body 2, and holding the second end portion of the tubular body 40 with the second holding portion 16. According to the fourth production method, the pressure portion 11 introduces pressurized gas into the lumen 41 of the tubular body 40 to apply internal pressure to the tubular body 40 and improve rigidity of the tubular body 40. The negative pressure portion 12 can thus efficiently suck and deliver the tubular body 40, into the second end 5 of the hollow portion 2 as a desired position, the tubular body 40 that is inhibited from being bent or deformed. In the fourth production method, the delivery device 1 preferably includes at least one of the first drive mechanism and the second drive mechanism described earlier. The first drive mechanism can move at least one of the pressure portion 11 and the first holding portion 15. The second drive mechanism can move at least one of the pressure portion 11, the first holding portion 15, and the first seal portion 21.

The fourth production method will be described with reference to FIGS. 7 to 14. FIGS. 7 to 14 are sectional views (partially side views) indicating the method for producing a catheter tube according to an embodiment of the present invention. In the fourth production method, reference can be made to the above description as to the hollow body 2, the pressure portion 11, the negative pressure portion 12, the first holding portion 15, the second holding portion 16, the first seal portion 21, the second seal portion 22, and the first drive mechanism or the second drive mechanism. FIGS. 7 to 14 do not depict the first drive mechanism or the second drive mechanism, although the delivery device 1 can include the first drive mechanism and the second drive mechanism as depicted in FIG. 6.

As depicted in FIG. 7, the first holding portion 15 holds the first end portion of the tubular body 40 (step 1). For easier introduction of pressurized gas into the tubular body 40, the lumen 41 of the tubular body 40 having been held by the first holding portion 15 has a sectional area that preferably corresponds to 90% or more of a sectional area of the lumen 41 of the tubular body 40 before being held by the first holding portion 15, that more preferably corresponds to 93% or more, and that further preferably corresponds to 95% or more.

As depicted in FIG. 8, the first seal portion 21 seals a gap between the first holding portion 15 and the tubular body 40 (step 2).

As depicted in FIG. 9, the delivery device 1 preferably includes the support portion 30 disposed between the hollow body 2 and the pressure portion 11 and supporting the tubular body 40, so that the support portion 30 supports part of the tubular body 40 in the longitudinal direction x1 (step 3). In the step 3, the tubular body 40 is more preferably supported at a position closer to the hollow body 2 rather than a center in the longitudinal direction x1. This prevents the second end 43 of the tubular body 40 from hanging down due to own weight.

As depicted in FIG. 10, the pressure portion 11 is connected to the first end 42 of the tubular body 40, and the pressure portion 11 introduces pressurized gas into the lumen 41 of the tubular body 40 (step 4).

As depicted in FIG. 10, the second seal portion 22 seals the gap between the hollow body 2 and the negative pressure portion 12 (step 5). The step 5 may be performed before any one of the steps 1 to 4, or may be performed after the step 4.

As depicted in FIG. 11, the pressure portion 11 and the tubular body 40 are moved toward the hollow portion 3 so as to dispose part of the tubular body 40 in the hollow portion 3 (step 6). Specifically, the first drive mechanism or the second drive mechanism preferably moves, in the extending direction x2 of the hollow portion 3, at least one of the pressure portion 11 and the first holding portion 15, or at least one of the pressure portion 11, the first holding portion 15, and the first seal portion 21. The tubular body 40 can thus be sucked and delivered smoothly into the hollow portion 3. The step 6 may be performed before or after the step 5.

As depicted in FIGS. 12 and 13, the negative pressure portion 12 sucks gas in the hollow portion 3 of the hollow body 2 to deliver the tubular body 40 toward the second end 5 of the hollow body 2 (step 7). In a case where the tubular body 40 is flexible, pressurized gas is preferably introduced into the lumen 41 of the tubular body 40 also in the step 7. In this case, the flexible tubular body 40 can be treated as the tubular body 40 entirely having more rigidity during delivery, for efficient delivery of the tubular body 40. The pressure portion 11 and the negative pressure portion 12 apply positive pressure and negative pressure that can be adjusted in accordance with rigidity and the length of the tubular body 40, as well as the diameter and the length of the hollow portion 3 in the hollow body 2. The applied positive pressure is preferably small for more efficient suction by the negative pressure portion 12, whereas the applied positive pressure is preferably large in order to linearly keep the tubular body 40 in the longitudinal direction x1. The applied positive pressure can also be adjusted in level in accordance with level of the applied negative pressure.

As depicted in FIG. 13, when at least the center of the tubular body 40 in the longitudinal direction x1 is disposed closer to the second end 5 rather than the first end 4 of the hollow body 2, the support portion 30 preferably stops support (step 8). The tubular body 40 having moved to the position is reduced in risk of hanging down due to own weight of the tubular body 40, and the tubular body 40 does not need to be supported by the support portion 30.

As depicted in FIG. 14, the second holding portion 16 holds the second end portion of the tubular body 40 (step 9).

Though not depicted, at least one of pressurization, heating, and stretching of the tubular body 40 may be performed after the step 9 (step 10). Alternatively, after the step 9, pressurized gas higher in pressure than the pressurized gas adopted in the step 4 may be introduced into the lumen 41 of the tubular body 40 so as to expand the tubular body 40 (step 11). As to stretching of the tubular body 40 in the step 10, reference can be made to description of the first to third production methods.

In the first to fourth production methods, pressurized gas introduced into the lumen 41 of the tubular body 40 during suction of gas from the tubular body 40 has pressure that may be kept constant or may be varied chronologically.

In the first to fourth production methods, power of sucking gas may be kept constant from start to end of suction, or may be varied chronologically.

In the first to fourth production methods, pressurized gas preferably starts being introduced before suction of gas from the tubular body 40. This reliably inhibits the tubular body 40 from being bent or deformed. In other words, the step 7 is preferably performed during the step 4 in the fourth production method.

This application claims the benefit of the priority date of Japanese patent application No. 2019-82880 filed on Apr. 24, 2019. All of the contents of the Japanese patent application No. 2019-82880 filed on Apr. 24, 2019 are incorporated by reference herein.

REFERENCE SIGNS LIST

1: Delivery device
2: Hollow body
3: Hollow portion
4: First end of the hollow body
5: Second end of the hollow body
11: Pressure portion
12: Negative pressure portion
15: First holding portion
16: Second holding portion
21: First seal portion
22: Second seal portion
25: First drive mechanism
26: Second drive mechanism
30: Support portion
31: Chuck piece
32: Third drive mechanism
40: Tubular body
41: Lumen
42: First end
43: Second end
44: Tapered portion
45: Small diameter portion
x1: Longitudinal direction of the tubular body
x2: Extending direction of the hollow portion
x: Horizontal direction
y: Vertical direction

The invention claimed is:

1. A method for producing a catheter tube, the method comprising sucking gas from a second end of a tubular body while introducing pressurized gas into a lumen of the tubular body from a first end of the tubular body, so that an internal pressure is applied to the lumen of the tubular body by introducing the pressurized gas, and the first end and the second end of the tubular body are delivered in a direction from the first end of the tubular body to the second end of the tubular body, while maintaining relative positions of the first and the second ends of the tubular body, by sucking the gas from the second end of the tubular body.

2. The method according to claim 1, the method further comprising
performing at least one of pressurization, heating, stretching, and blow molding of the tubular body to form the tubular body into a predetermined shape.

3. The method according to claim 1, wherein
the second end of the tubular body is sealed, and
the method further comprises:
performing at least one of pressurization, heating, stretching, and blow molding of the tubular body to form the tubular body into a predetermined shape; and
cutting a second end portion of the tubular body to allow the lumen at the second end to communicate with an outside of the tubular body.

4. The method according to claim 1, wherein a second end portion of the tubular body is sealed.

5. The method according to claim 1, wherein the tubular body has a portion smaller in outer diameter than the first end of the tubular body, the portion being located closer to the second end rather than the first end of the tubular body.

6. The method according to claim 1, further comprises arranging the tubular body and a device configured to deliver the tubular body, wherein
the device comprises:
a hollow body having a hollow portion extending from a first end to a second end of the hollow body;
a pressure portion disposed at the first end of the hollow body and connectable to the tubular body so as to introduce the pressurized gas into the lumen of the tubular body; and
a negative pressure portion disposed at the second end of the hollow body and connected to the hollow body so as to suck gas from the hollow portion of the hollow body, and
the pressure portion is connected to the tubular body.

7. The method according to claim 6, wherein
the device further comprises
a first holding portion disposed between the pressure portion and the hollow body, the first holding portion holding a first end portion of the tubular body, and
a second holding portion disposed between the hollow body and the negative pressure portion, the second holding portion holding a second end portion of the tubular body delivered toward the second end of the hollow body.

8. The method according to claim 7, wherein
each of the first holding portion and the second holding portion includes one or more chuck pieces.

9. The method according to claim 7, wherein
the device further comprises
a first seal portion disposed between the pressure portion and the first end portion of the tubular body, the first seal portion sealing a gap between the pressure portion and the tubular body, and
a second seal portion disposed between the hollow body and the negative pressure portion, the second seal portion sealing a gap between the hollow body and the negative pressure portion.

10. The method according to claim 9, wherein
the device further comprises a second drive mechanism configured to move at least one of the pressure portion, the first holding portion, and the first seal portion in an extending direction of the hollow portion.

11. The method according to claim 9, wherein the method includes:
holding the first end portion of the tubular body with the first holding portion;
sealing a gap between the first holding portion and the tubular body with the first seal portion;
connecting the pressure portion to the first end of the tubular body and introducing the pressurized gas into the lumen of the tubular body with the pressure portion;

sealing the gap between the hollow body and the negative pressure portion with the second seal portion;

moving the pressure portion and the tubular body toward the hollow portion so that a part of the tubular body is disposed in the hollow portion;

sucking the gas in the hollow portion of the hollow body with the negative pressure portion so that the tubular body is delivered toward the second end of the hollow body;

and holding the second end portion of the tubular body with the second holding portion.

12. The method according to claim 7, wherein
the device further comprises a first drive mechanism configured to move at least one of the pressure portion and the first holding portion in an extending direction of the hollow portion.

13. The method according to claim 6, wherein
in the sucking gas from the second end of the tubular body, at the second end of the tubular body, the gas sucked by the negative pressure portion is larger in amount than gas discharged from the lumen of the tubular body.

14. The method according to claim 6, wherein
a difference between a diameter of the hollow portion at the second end of the hollow body and an outer diameter at the second end of the tubular body is larger than a difference between a diameter of the hollow portion at the first end of the hollow body and a maximum outer diameter of the tubular body.

15. The method according to claim 6, wherein
the device further comprises a support portion disposed between the hollow body and the pressure portion, the support portion supporting the tubular body.

16. The method according to claim 6, wherein
the hollow body comprises a metal mold for blow molding.

17. The method according to claim 1, wherein the tubular body has the lumen penetrating from the first end of the tubular body to the second end of the tubular body.

18. The method according to claim 1, the method further comprises:

holding a second end portion of the tubular body outside the tubular body after sucking gas from the second end of the tubular body while introducing pressurized gas into the lumen of the tubular body from the first end of the tubular body.

19. The method according to claim 1, the method further comprises:

arranging the tubular body and a device configured to deliver the tubular body, the device comprising a hollow body having a hollow portion extending from a first end to a second end of the hollow body, the hollow portion being provided to penetrate from the first end to the second end of the hollow body, the hollow portion having a suction port at the second end, the suction port having an inner diameter larger than an outer diameter of the tubular body, before sucking gas from the second end of the tubular body while introducing pressurized gas into the lumen of the tubular body from the first end of the tubular body.

20. The method according to claim 1, wherein
the tubular body is delivered into a hollow portion of a hollow body, the hollow portion extending from a first end to a second end of the hollow body.

* * * * *